United States Patent [19]
Cabral et al.

[11] Patent Number: 6,102,567
[45] Date of Patent: *Aug. 15, 2000

[54] X-RAY BONE DENSITOMETRY USING A VERTICALLY SCANNING GANTRY

[75] Inventors: Richard E. Cabral, Tewksbury; Jay A. Stein, Framingham, both of Mass.

[73] Assignee: Hologic, Inc., Waltham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/649,280

[22] Filed: May 17, 1996

[51] Int. Cl.$^7$ ........................................... H05G 1/02
[52] U.S. Cl. .............................. 378/197; 378/55; 378/146
[58] Field of Search .................................. 378/146, 196, 378/197, 57, 55, 54

[56] References Cited

U.S. PATENT DOCUMENTS

| | | |
|---|---|---|
| Re. 34,511 | 1/1994 | O'Neill et al. . |
| 3,101,407 | 8/1963 | Shipman ................................. 378/146 |
| 3,639,764 | 2/1972 | Olson et al. . |
| 4,590,378 | 5/1986 | Platz . |
| 4,696,025 | 9/1987 | Taylor ..................................... 378/146 |
| 4,788,429 | 11/1988 | Wilson . |
| 4,811,373 | 3/1989 | Stein . |
| 4,947,414 | 8/1990 | Stein . |
| 5,040,199 | 8/1991 | Stein ........................................ 378/54 |
| 5,132,995 | 7/1992 | Stein . |
| 5,148,455 | 9/1992 | Stein . |
| 5,155,756 | 10/1992 | Pare et al. . |
| 5,165,410 | 11/1992 | Warne et al. . |
| 5,228,068 | 7/1993 | Mazess . |
| 5,283,823 | 2/1994 | Morris . |
| 5,287,546 | 2/1994 | Tesic et al. . |
| 5,305,368 | 4/1994 | Bisek et al. . |
| 5,432,834 | 7/1995 | Gershman . |
| 5,475,730 | 12/1995 | Galando . |

FOREIGN PATENT DOCUMENTS

WO94/06351  3/1994  WIPO .

OTHER PUBLICATIONS

Oldelft "Amber" Brochure (undated).
Osteometer DTX–300 brochure, undated.

*Primary Examiner*—Craig E. Church
*Attorney, Agent, or Firm*—Cooper & Dunham LLP

[57] ABSTRACT

The present invention provides a system that reduces the complexity of existing dual energy x-ray equipment which typically requires more complicated mechanisms to measure bone density, to a system with a single axis of mechanical motion and with a patient providing repositioning motions. This configuration allows for a much more compact design and smaller equipment "footprint," thus taking up less floor space in examination rooms and allowing for multiple uses of one room. The system of the present invention eliminates the need for a patient support table which can affect x-ray transmission because of the thickness and construction of the table which are dictated by the weight of the patient. The system includes a main cabinet or gantry enclosure which contains an x-ray source and ancillary support electronics and mechanisms. An extension arm positions a detector assembly on a side of the patient opposite to the source assembly and fixes the distance between the source and detector assemblies. The source and detector assemblies are capable of making dual energy bone measurements. The source assembly, detector assembly and extension arm form a gantry and the source assembly and detector assembly are confined to move in unison in a vertical scanning motion. A drive mechanism in conjunction with a precision guide rail provides a stable, smooth vertical scanning motion of the gantry. A counter balance system is provided to reduce the forces required to move the gantry. In addition, the extension arm may either fold or retract into the main cabinet to reduce the system volume when not in use.

51 Claims, 3 Drawing Sheets

X-RAY BONE DENSITOMETRY USING A VERTICALLY SCANNING GANTRY

BACKGROUND OF THE INVENTION

1. Field of the Invention

This present invention relates to a system and method of measuring bone density. More particularly, the present invention relates to a method of scanning patients in a standing position using a vertical scanning technique instead of the conventional method with the patient lying down.

2. Description of the Related Technology

X-rays or gamma-rays can be used to measure the density and distribution of bone in the human body in order to help health professionals assess and evaluate projected bone mineral density, which in turn can be used to monitor age-related bone loss that can be associated with diseases such as osteoporosis. Additionally or alternatively, similar procedures can be used to measure non-bone related body content such as body fat and muscle.

In bone densitometry, a patient typically is placed on a table such that the patient's spine extends along the length of the table, along a direction that can be called the Y-axis in Cartesian coordinates. For a supine patient, the left and right sides are in a direction typically called the X-axis. A source at one side of the patient transmits radiation through the patient to a radiation detector at the other side. The source and the detector typically are mechanically linked by a structure such as a C-arm to ensure their alignment along a source-detector axis which is transverse (typically perpendicular) to the Y-axis. Both x-ray tubes and isotopes have been used as a source of the radiation. In each case, the radiation from the source is collimated to a specific beam shape prior to reaching the patient to thereby restrict the field of x-ray or gamma radiation to the predetermined region of the patient opposite which are located the detectors. In the case of using x-rays, various beam shapes have been used in practice including fan beam, pencil beam and cone or pyramid beam shapes. When a fan beam is used, typically the beam conforms to a beam plane which is transverse (e.g., normal) to the Y-axis. Stated differently, the beam is wide in a plane that includes the X-axis and thin along the Y-axis. The shape of the beam and the shape of the detector system correspond. The detector in a fan beam system typically is an elongated array of detector elements arranged along a line or an arc. By means of mechanically moving the C-arm and/or moving the table, a region of interest in a patient on the table can be scanned with the radiation. Typical regions of analysis in bone densitometry include the spine, hip and forearm scanned individually. They can be covered individually within a reasonable time by a fan beam that has a relatively narrow angle in a single pass or, alternatively, by a pencil beam scanning a raster pattern.

Another analysis region is referred to as "whole body" in which the entire patient body is scanned and analyzed for bone density and possibly also for "body composition" or the percentages of fat and muscle in the body.

X-ray bone densitometry systems have been made by the owner of this application under the tradenames QDR-2000+, QDR-2000, QDR-1500, QDR-1000plus, QDR-1000, QDR-4500A, QDR-4500SL, QDR-4500C, and QDR-4500W. The following commonly owned U.S. patents and pending applications pertain to such systems and are hereby incorporated by reference herein: Ser. Nos. 08/345,069 and 08/465,736; U.S. Pat. Nos. 4,811,373, 4,947,414, 5,040,199, 5,132,995, 5,148,455, 5,432,834, and 5,155,756; and Re. 34,511 and 5,165,410 (each assigned on its face to Medical & Scientific Enterprises, Inc. but now commonly owned). Other bone densitometry systems are believed to have been made by the Lunar Corporation of Madison, Wis. (see, e.g., the system which is believed to be offered under the tradename Expert and U.S. Pat. Nos. 5,228,068, 5,287,546 and 5,305,368).

The system and method according to the present invention provides a cost effective alterative to practitioners from, for example, higher priced wide fan beam, rotating C-arm scanning systems such as the QDR-4500A product.

SUMMARY

The present invention provides a system that reduces the complexity of existing equipment which typically require more complicated mechanisms to measure bone density, to a system with a single axis of mechanical motion and with a patient providing other repositioning motions. This configuration allows for a much more compact design and smaller equipment "footprint", thus taking up less floor space in examination rooms and allowing for multiple uses of one room. The system of the present invention eliminates the need for a patient support table which can affect x-ray transmission because of the thickness and construction of the table which is dictated by the weight of the patient.

Using the system of the present invention A/P (P/A) spine, hip, wrist, forearm, hand and lateral spine scanning can be performed. Generally, the system in the present invention uses x-rays having a narrow fan beam to scan patients for bone measurements, such as bone density and/or bone shape, and imaging using vertical, single pass scans. The patient is positioned in front of a vertical scanning window and subsequently repositioned relative to the scanning window depending on which scan is being performed. For example, the patient can face one way to obtain A/P spine images and turn 90 degrees to obtain lateral spine images.

In the preferred embodiment, the system includes a main cabinet or gantry enclosure which contains an x-ray source and ancillary support electronics and mechanisms. An extension arm positions a detector assembly on a side of the patient opposite to the source assembly and fixes the distance between the source and detector assemblies. The source assembly, detector assembly and extension arm form a gantry. The radiation source assembly and detector assembly are confined to move in unison in a vertical scanning motion. A drive mechanism in conjunction with a precision guide rail provides a stable, smooth vertical scanning motion of the gantry. A counter balance system is provided to reduce the forces required to move the gantry. The length of the vertical scanning motion ranges between a position matching the lowest hip position of the shortest 95th percentile of patients and a position matching the highest spine position of the tallest 95th percentile of patients during a lateral spine scan. In addition, the extension arm may either fold or retract into the main cabinet to reduce the system volume when not in use.

The system of the present invention may also include various patient stabilizing aids and/or a laser positioning systems to aid in patient positioning relative to the source and detector. For example, a stabilizing aid may include a cabinet mounted, x-ray translucent cradling fixture in conjunction with VELCRO® straps to position and stabilize the patient relative to the x-ray beam.

BRIEF DESCRIPTION OF THE DRAWINGS

Preferred but non-limiting embodiments of the invention are described hereinbelow with reference to the drawings wherein.

DETAILED DESCRIPTION

The system 10 of the present invention typically uses x-rays having a narrow angle fan beam to scan patients for bone density measurements and imaging using vertical, single pass scans. The system 10 provides mechanical scanning motion in one direction, and the patient provides repositioning motions. As a result, the system configuration provides a compact design and a smaller equipment "foot print" to occupy less floor space in, for example, examination rooms.

Figure 1:
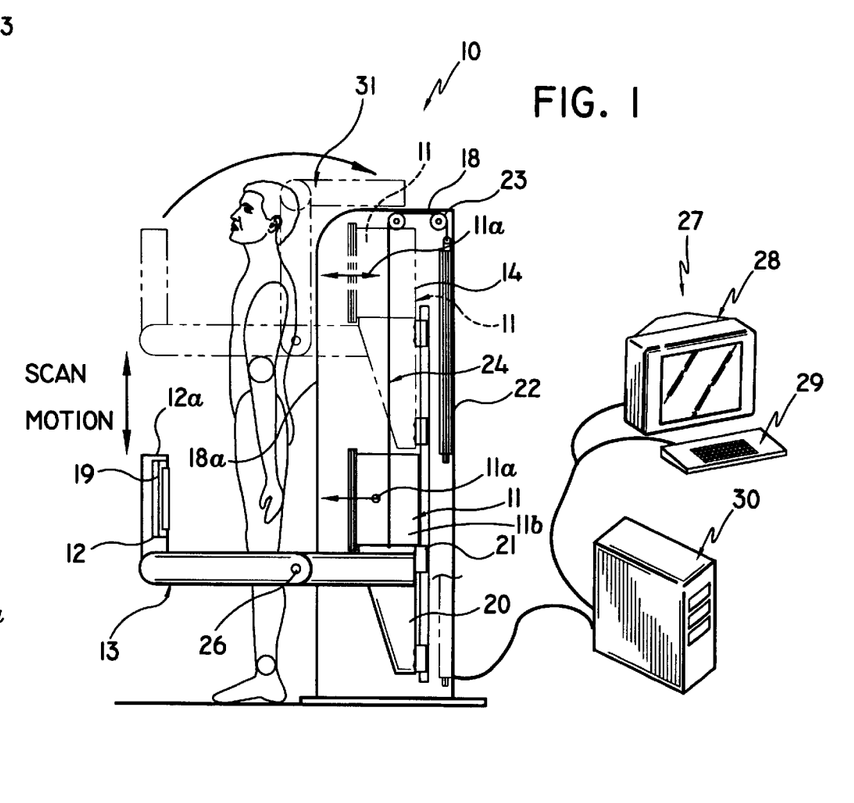
FIG. 1 is a side elevation, partly in section, of a scanning system according to the present invention, showing the motion of a radiation source assembly and a radiation detector assembly relative a system enclosure.

Referring to FIG. 1, the scanning system 10 includes a gantry enclosure 18, a gantry that includes a source assembly 11, and a detector assembly 12, and an operator control station 27 that controls the operation of the gantry, and the source and detector assemblies and processes scan data detected by the detector assembly 12 to obtain bone measurement data and to transform the bone measurement data into image data for display or other purposes. The source assembly and detector assembly are capable of making dual energy x-ray measurements. The operator control station 27 also acts as an operator interface to the bone measuring equipment and includes a computer 30 connected to a keyboard 29 and a monitor 28. The computer 30 has a processor, memory (e.g., volatile and non-volatile memory) and stored system and application programs. The operator console station 27 may also include an optional printer and associated communication hardware to provide hard copies of measured bone density images and/or bone density and other data. The computer 30 may be a PC type computer or a custom design computer system to provide computer control of the movements of the gantry and data acquisition and processing. Alternatively, the operator console station 27 may be a laptop type computer which would replace the monitor 28, keyboard 29 and computer 30.

As noted, the operator console station 27 controls the operation of the source and detector assemblies 11 and 12, and processes the scan and position data received from the detector assembly into forms more useful for diagnostic purposes, such as into patient images and reports. The source assembly 11 and the detector assembly 12 are connected to the gantry enclosure 18 at a fixed distance apart and configured to move in unison to maintain the source-detector distance and alignment, so that radiation from the source assembly can impinge on the detector assembly along straight raypaths.

The source assembly 11 has a radiation source 11a, such as a single energy or a dual energy x-ray source, positioned within a source enclosure 14 and an assembly drive system 25. The radiation source 11a is preferably an x-ray source configured to emit dual-energy x-rays. That is, the radiation source 11a is a dual-energy (DE) pulse system that is synchronized to the alternating current system power source. A more detailed discussion of such dual energy x-ray sources can be found in commonly owned U.S. Pat. No. 5,432,834 to Gershman, and U.S. Pat. Nos. 4,947,414 and 4,811,373 both to Stein, all of which are incorporated herein in their entirety by reference. Although the preferred embodiment contemplates using an x-ray source with an output that alternates between two energy levels, use of a polychromatic source in combination with a detector assembly that discriminates two energy levels is also contemplated.

Figures 2, 3:
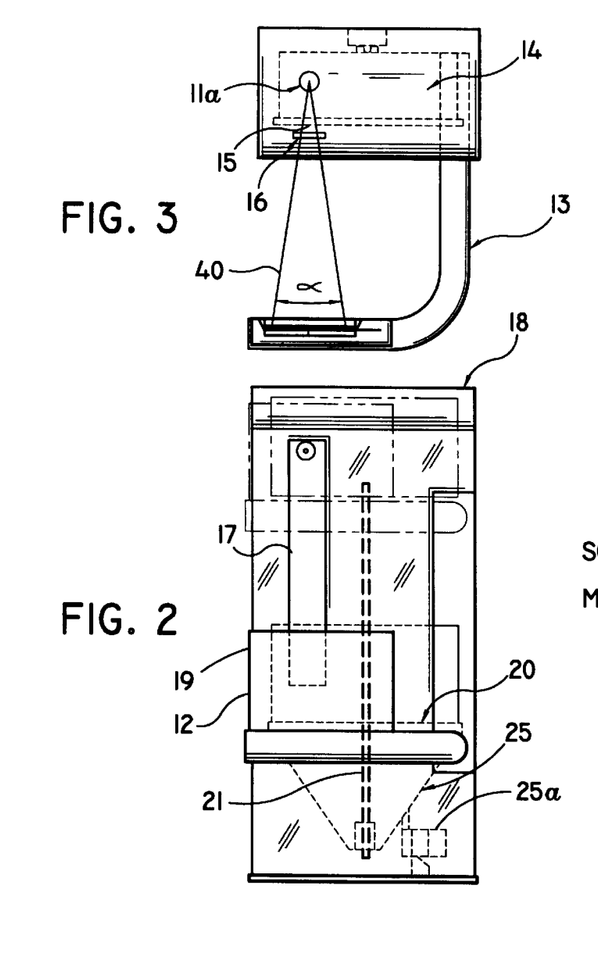
FIG. 2 is a front elevation of the scanning system of FIG. 1.
FIG. 3 is a top plan view of the scanning system of FIG. 1, illustrating a fan beam of x-rays being radiated from an x-ray radiation source assembly toward an x-ray radiation detector assembly.

The source enclosure 14 includes a transmission window 15 (FIG. 3) which acts as a collimator and is located on the cover of the enclosure 14. The transmission window 15 is positioned between source 1a and the patient and has one or more selectable slits machined or otherwise formed to allow the passage of radiation (e.g., x-rays) from source 11a through a slit toward the patient. The transmission window 15 is preferably made of an x-ray opaque material, such as lead or tungsten, of sufficient thickness to substantially block the passage of x-rays through portions of the window 15 other than through the slits. For example, the transmission window 15 has a 64 mm by, e.g., 1 mm collimator slit positioned an appropriate distance from the focal spot in source 11a and is suitably aligned therewith. The radiation from the source 11a passes through a selected slit in the transmission window and forms a fan shaped beam 11a of, for example x-rays, as seen in FIG. 3. The angle subtended by the fan-shaped beam 40 and the distance between its origin at the focal spot of an x-ray tube and the patient are selected so that the beam would not cover the entire cross-section of a typical adult patient at any one time but would cover only a selected portion of that width.

The fan-shaped beam 40 has a narrow fan angle "α" which ranges from between about 0.2 degrees and about 30 degrees. Preferably, the fan angle is 17 degrees. Of course, the x-ray beam 40 not only has width along a horizontal axis but also has a thickness along a vertical axis that is defined by the slit in transmission window 15 which is at a distance of, e.g., 83 cm from the origin (the focal spot) of the beam 40.

As noted, the computer processes scan data detected by the detector assembly 12. The scan data is derived from scan lines which are defined by the portion of the patient imaged with the fan beam 40 and detected with the detector 19 over a sampling time interval. That is, a scan line includes the width and thickness of the x-ray beam over which data is collected during one sampling time interval. While the term scan line is used, it should be clear than this "line" in fact is a rectangle that has both a width in the horizontal direction and length in the vertical direction. A complete scan consists of one or a set of adjacent (and somewhat overlapping in space) scan passes obtained over a period of time such that the entire region of interest has been measured. The transmission window 15 directs radiation (e.g., x-rays) from the source 11a through a redefining aperture system 16 which also serves a collimating function.

Preferably, the source enclosure is shielded to prevent radiation (e.g., x-rays) from exiting the source enclosure 14 except through the transmission window 15. The source enclosure is also constructed to electrically isolate the enclosure to minimize the influence of spurious signals on the source 11a and to prevent electrical interferences from being emitted through the source enclosure.

As noted, radiation from the source 11a is directed toward the redefining aperture system 16 which is positioned between an outer wall 18a of the gantry enclosure and the source enclosure 14, as seen in FIG. 3. The redefining aperture system 16 may include a single aperture or multiple apertures that are configured to redefine the rays emitted by the source 11a. For example, if a fan shaped x-ray beam is radiated from the source enclosure 14 to scan a patient, the redefining aperture system 16 may be configured by the operator to alter the beam width so that the beam is appropriately sized for the particular scan being performed. Radiation then passes through a radiation transparent window 17 mounted to the outer wall 18a of the gantry enclosure 18. Preferably, the radiation transparent window 17 is made of a material which does not substantially alter or otherwise affect the radiation from the source. For example, the window may be fabricated from polycarbonate (LEXAN®).

The source enclosure 14 is supported in the gantry enclosure 18 by shelf structure 20 which is part of the gantry. The shelf support structure 20 is mounted to an assembly drive system 25 and moves within the gantry enclosure 18 vertically along a guide rail system 21. The extension arm 13 is connected to the shelf support structure 20 so that the detector enclosure 12a and the source enclosure 14 move in unison when the shelf support structure 20 is moved along the guide rail system 21. The weight of the combination of the shelf support structure, source enclosure, detector enclosure 12a, and extension arm 13 is balanced by counterweights 22 via redundant pulleys 23 and cables 24 to minimize driving forces and to ensure smooth movement of the source and detector assemblies. The counterweights are attached to the shelf structure 20 at the source assembly/shelf support structure center of gravity so as to minimize the moment loads applied to the guide rail system 21. The redundant cables 24 and pulleys 23 are provided to insure that in the event a single cable or pulley fails, support for the gantry including the source and detector assemblies will be maintained even though the gantry will not operate. A drive mechanism 25a, such as a stepper motor, is then used to propel the gantry in the vertical direction to scan a patient at a predetermined rate. This rate can be any constant or variable speed depending on the scan being obtained. For example, if a lateral spine scan is being performed the scan rate may be 2.5 centimeters per second (cm/sec.). As another example, if an A/P spine scan is being performed, the scan rate may be 1.0 cm/sec.

The detector assembly 12 includes a detector housing 12a mounted to an extension arm 13. The extension arm 13 has a predefined length of about 32 inches to fix the distance between the radiation source and detector. The detector enclosure has a radiation detector 19 mounted therein.

The radiation detector 19 is preferably an array of detector elements, e.g., 64 elements, arranged in a linear configuration extending along the horizontal axes. The radiation detector 19 is, e.g., about 10 inches long in the horizontal direction and subtends a fan angle of about 17 degrees (i.e., a 0.16 inch detector-to-detector spacing). Preferably, the detector elements that make up the array are silicon photodiodes coupled with a scintillation material, and they are fixed with respect to radiation source 11a. For example, the radiation detector is positioned about 32 inches from the origin of the beam. Other types of detector elements that are known in x-ray technology are also contemplated. Each detector element responds to x-rays at respective angular positions within a fan beam of x-rays and provide scan data to computer 30 in operator console station 27.

The extension arm 13 in the embodiment seen in FIG. 3 is preferably an L-shaped structure that employs a pivot joint 26 in order to fold the arm onto the top of the machine into a stowed position 31 so as to reduce the stored volume of the system 10. The extension arm 13 is rotated when the shelf support structure 20 is moved to a maximum vertical position, as seen in phantom in FIG. 1. Other methods may be employed to store the arm structure substantially within the gantry enclosure 18 when the system 10 is not in use or when shipping the system. One example of an alternative embodiment is a telescopic arm that retracts into the gantry enclosure 18, seen in FIG. 8.

Data acquisition, processing and image display are performed using known processes which are discussed in, for example, copending patent applications Ser. No. 08/465,736 filed Jun. 6, 1995 and Ser. No. 08/345,069 filed Nov. 25, 1994 both of which are incorporated herein in their entirety by reference. Generally, the computer which is coupled to the assembly drive system 25 in the gantry enclosure 18, the source 11a and the radiation detector 19, controls the real-time acquisition of scan data coordinated with the movement of the gantry. The radiation detector 19 supplies radiation measurements (scan data) to the computer 30 in the operator console station 27, where the measurements are collected, stored and preliminarily processed. As noted, the computer processes the scan data using known bone measurement data processing techniques so that data and images processed by the computer are supplied to the monitor 28 and in some instances stored in memory for later use. If a printer is connected to the computer, a hardcopy of the data may be obtained for purposes and in a manner similar to those in the earlier systems.

Figure 4:
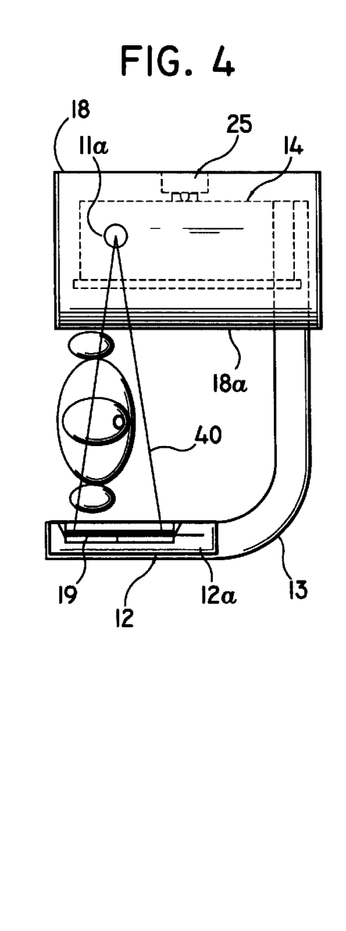
FIG. 4 is a top plan view of the scanning system of FIG. 1, illustrating a patient positioned for a lateral spine scan.
Figure 5:
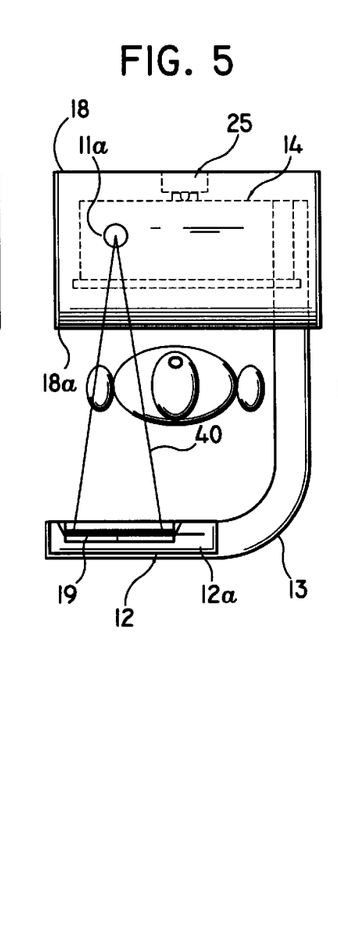
FIG. 5 is a top plan view of the scanning system of FIG. 1, illustrating a patient positioned for a left hip scan.
Figure 6:
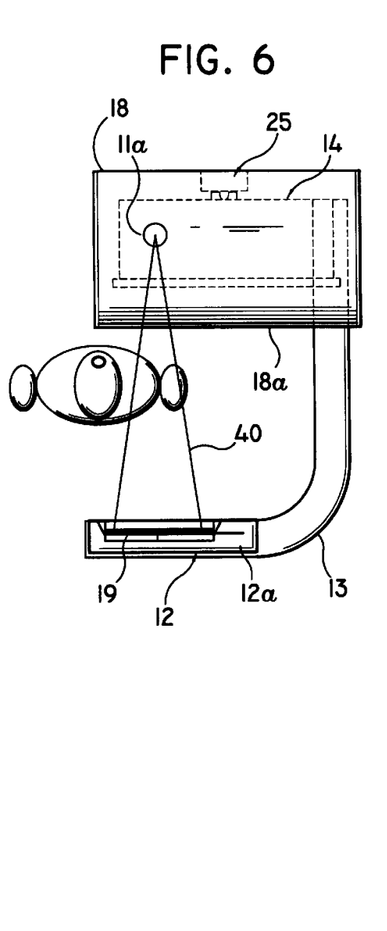
FIG. 6 is a top plan view of the scanning system of FIG. 1, illustrating a patient positioned for a right hip scan.
Figure 7:
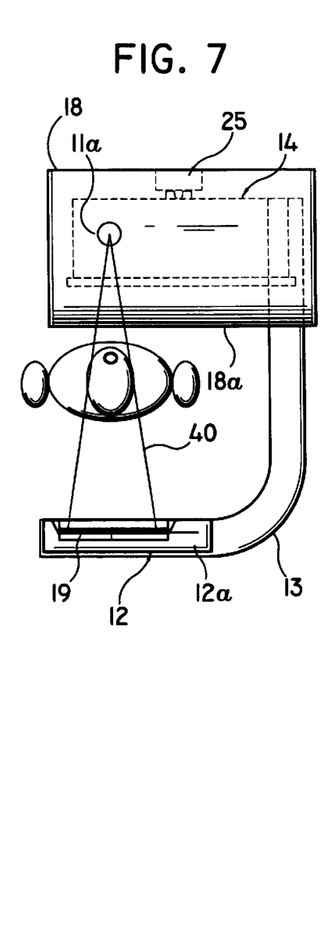
FIG. 7 is a top plan view of the scanning system of FIG. 1, illustrating a patient positioned for an A/P spine scan.

Referring to FIGS. 4–7 various patient scanning positions are shown. The system 10 of the present invention is capable of performing most scanning modalities to obtain bone density measurements, so that the scanning positions seen in FIGS. 4–7 are only exemplary. FIG. 4 illustrates the positioning of a patient for a lateral spine bone density measurement, wherein the patient is positioned with the shoulders along a line substantially perpendicular to the detector assembly 12. The patient's arms may be raised to be out or mostly out of the beam path. FIGS. 5 and 6 illustrate the positioning of the patient for left hip and right hip bone density measurements, respectively, wherein the patient's shoulders are along a line substantially parallel to the detector assembly 12. Again, the patient's arms may be moved out of the beam path. FIG. 7 illustrates the positioning of the patient for an A/P (anterior/posterior) spine bone density measurement, wherein the patient's shoulders are again along a line substantially parallel to the detector assembly 12.

Figure 8:
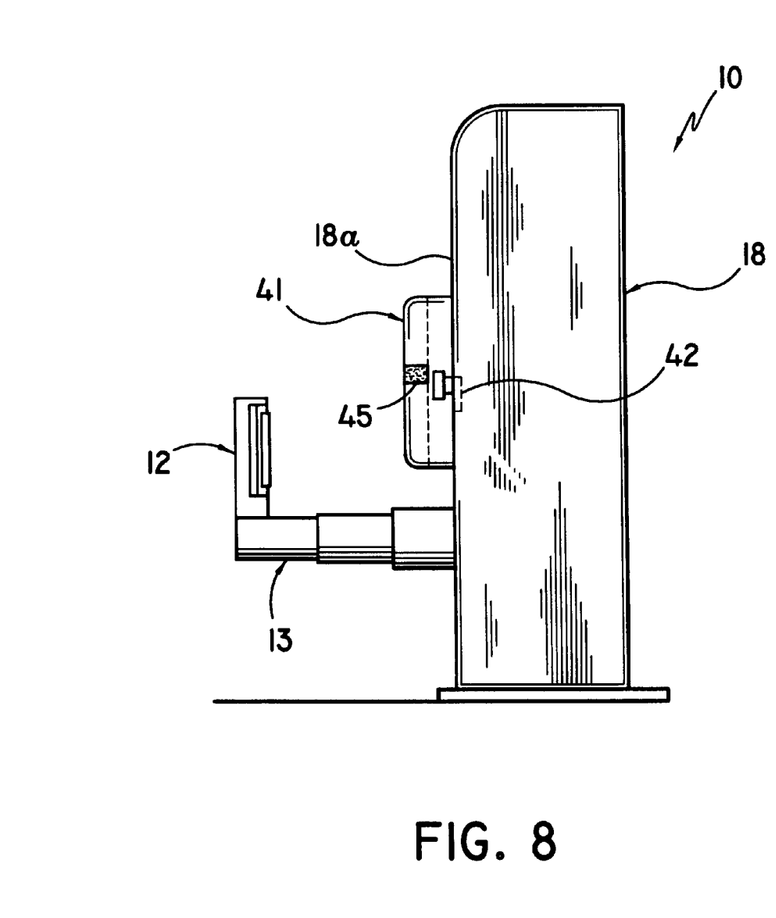
FIG. 8 is a side plan view of a scanning system similar to FIG. 1, illustrating a patient stabilizing apparatus secured thereto.
Figure 9:
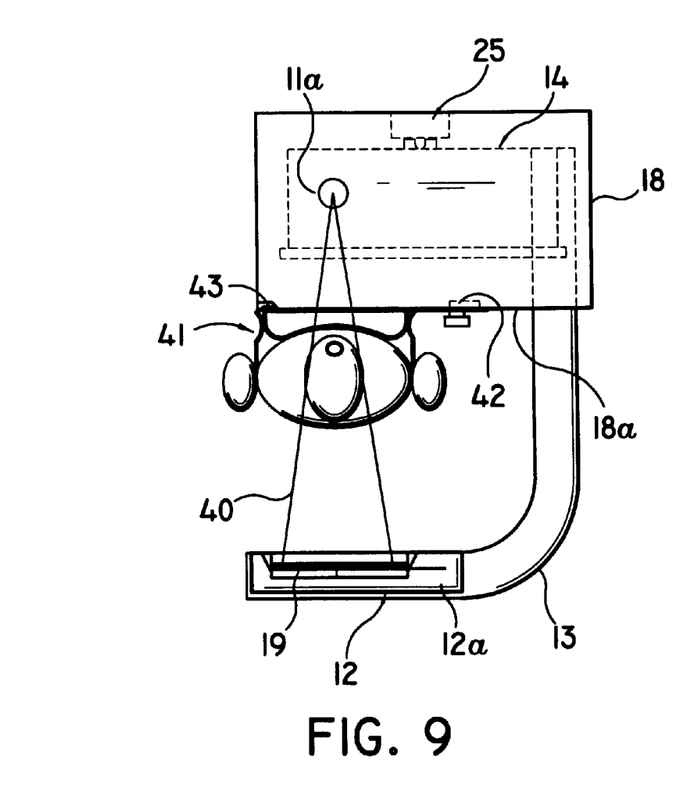
FIG. 9 is a top plan view of the scanning system of FIG. 9, illustrating a patient secured to the patient stabilizing apparatus for an A/P spine scan.

FIGS. 8 and 9 illustrate an exemplary embodiment of a patient stabilizing apparatus 41 which is removably mounted to the outer wall 18a of the gantry enclosure 18 using locking member 42 and retaining brackets 43. The apparatus is secured to the gantry enclosure by inserting the retaining brackets into slots (not shown) in the gantry cabinet 18 and inserting the locking member 42 into a corresponding slot in the gantry enclosure and turning the locking member. A belt 44 preferably having VELCRO® connection portions that mate with VELCRO® connection portions 45 secured to the patient stabilizing apparatus, is used to secure the patient to the patient stabilizing apparatus.

The system and method according to the present invention provides a cost effective choice to practitioners as compared to, for example, higher priced wide fan beam, rotating C-arm scanning systems. Further, the system of the present invention performs different bone measuring scans, e.g., the lateral and A/P spine scans, efficiently because the patient is standing, and to perform different scans the patient can simply change position relative to the source assembly. In addition, because the patient is standing the weight of the patient does not have to be accounted for when designing the system and selecting materials and components for the system. As a result, more economical materials and components may be used when manufacturing the system. For example, materials may be used which minimize x-ray attenuation and irregularities which provides higher quality bone density measurements.

It will be understood that various modifications can be made to the embodiments of the present invention herein disclosed without departing from the spirit and scope thereof. For example, various drive mechanisms may be employed to move the shelf support structure, or to retract or otherwise reduce the area occupied by the arm structure when the system is not in use. The system is also capable of performing many different bone density measurements including, but not limited to, forearm, wrist, hand and other appendage bone density measurements. Further, various patient positioning aids may be used for locating and stabilizing the patient in the correct position relative to the source and detector assemblies for a particular scan acquisition, and various types of computers or processors may be utilized to perform data acquisition and processing. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A dual energy x-ray apparatus for vertically scanning a patient, which comprises:
    an enclosure;
    a gantry positioned at least partially in said enclosure and vertically movable within said enclosure between an upper position and a lower position, said gantry including a source assembly and a detector assembly which are spaced from each other by patient space and are configured to move in a scanning motion in unison when said gantry is vertically moved, wherein said source assembly is positioned in said enclosure and said detector assembly is positioned outside said enclosure, and wherein said source assembly includes an x-ray source and transmission window and is configured to emit a fan beam of x-ray radiation that includes high energy x-rays and low energy x-rays, the transmission window configured to serve as a collimator and wherein said detector assembly receives said fan beam of x-ray radiation and produces, from said high and low energy x-rays, dual energy detected x-ray outputs comprising high energy detected x-ray outputs and low energy x-ray detected outputs; and
    a redefining aperture also configured to serve as a collimator and positioned between an outer wall of the enclosure and the source assembly for selectively redefining the fan beam emitted by the x-ray source and collimated by the transmission window.

2. The apparatus according to claim 1 further comprising an operator control station connected to said source and detector assemblies and said gantry to coordinate movement of said gantry at a predefined rate while radiating said fan beam of x-rays from said source assembly so as to scan a selected portion of a patient positioned between said source and detector assemblies.

3. The apparatus according to claim 2, wherein said operator control station receives scan data from said detector assembly and processes said scan data to determine bone density.

4. The apparatus according to claim 1, wherein said source assembly is located within said enclosure and said detector assembly is external to said enclosure.

5. The apparatus according to claim 1, wherein said detector assembly includes a detector positioned within a detector housing.

6. The apparatus according to claim 5, wherein said detector includes an array of detectors arranged in a linear configuration extending along linear and horizontal axes.

7. The apparatus according to claim 1, wherein said fan beam has an angle ranging from between about 2 degrees and 30 degrees.

8. The apparatus according to claim 7, wherein said fan beam has an angle of 17 degrees.

9. The apparatus according to claim 1 further comprising a patient stabilizing apparatus removably mounted to said enclosure between said source assembly and said detector assembly, said patient support apparatus being configured to secure a position of the patient relative to said source and detector assemblies.

10. The apparatus according to claim 9, wherein said patient stabilizing apparatus is made of an x-ray translucent material.

11. A dual energy x-ray apparatus for vertically scanning a patient, which comprises:
    an enclosure;
    a gantry positioned at least partially in said enclosure and vertically movable within said enclosure between an upper position and a lower position, said gantry including a source assembly positioned within said enclosure and a detector assembly mounted to an extension arm extending from said enclosure such that said detector assembly is positioned outside said enclosure, said source and detector assemblies are configured to move in unison when said gantry is vertically moved to scan with a fan beam of x-ray radiation a selected portion of a patient who is between the source and detector assemblies, the source assembly including an x-ray source and a transmission window, the transmission window configured to serve as a collimator, wherein said source assembly is arranged in a fixed relationship with said detector assembly and emits said fan beam of x-ray radiation that includes high energy x-rays and low energy x-rays toward said detector assembly such that when said fan beam of x-ray radiation from said source assembly impinges said detector assembly said detector assembly produces, from said high and low energy x-rays, dual energy scan data comprising high energy detected x-ray data and low energy x-ray detected data; and
    a redefining aperture also configured to serve as a collimator and positioned between an outer wall of the enclosure and the source assembly for selectively redefining the fan beam emitted by the x-ray source and collimated by the transmission window.

12. The apparatus according to claim 11 further comprising an operator control station connected to said source and detector assemblies and said gantry to coordinate movement of said gantry at a predefined rate while radiating said fan beam of x-rays from said source assembly so as to scan a selected portion of a patient positioned between said source and detector assemblies.

13. The apparatus according to claim 12, wherein said operator control station receives scan data from said detector assembly and processes said scan data to determine bone density.

14. The apparatus according to claim 11, wherein said extension arm is configured for storage in said enclosure when said apparatus is not in use.

15. The apparatus according to claim 11, wherein said extension arm has a hinge for folding said extension arm into said enclosure when said gantry is in said upper position.

16. The apparatus according to claim 11, wherein said extension arm is a telescopic arm that retracts into said enclosure.

17. A dual energy x-ray apparatus for vertically scanning a patient, which comprises:
 an enclosure;
 a gantry positioned at least partially in said enclosure and vertically movable within said enclosure between an upper position and a lower position, said gantry including a source assembly and a detector assembly spaced from each other such that said source assembly and detector assembly are configured to move in unison when said gantry is vertically moved, wherein said source assembly is positioned in said enclosure and said detector assembly is positioned outside said enclosure, and wherein said source assembly includes an x-ray source positioned within a source housing and a transmission window located on an outer wall of said source housing, the transmission window configured to serve as a collimator, said source assembly being configured to emit a fan beam of x-ray radiation that includes high energy x-rays and low energy x-rays through said transmission window toward said detector assembly, and wherein said detector assembly receives said x-ray radiation and produces, from said high and low energy x-rays, dual energy scan data comprising high energy x-ray data and low energy x-ray detected data;
 a redefining aperture also configured to serve as a collimator and positioned between an outer wall of the enclosure and the source assembly for selectively redefining the fan beam emitted by the x-ray source and collimated by the transmission window; and
 an operator control station connected to said source and detector assemblies and said gantry to coordinate movement of said gantry at a predefined rate while emitting said fan beam of x-ray radiation from said source assembly so as to scan a selected portion of a patient positioned between said source and detector assemblies, and said operator control station receives said scan data from said detector assembly and processes said scan data to determine bone density.

18. The apparatus according to claim 17, wherein said detector assembly is secured to an extension arm extending from said enclosure.

19. The apparatus according to claim 18, wherein said extension arm is configured for storage in said enclosure when said apparatus is not in use.

20. The apparatus according to claim 18, wherein said extension arm has a hinge for folding said extension arm into said enclosure when said gantry is in said upper position.

21. The apparatus according to claim 18, wherein said extension arm is a telescopic arm that retracts into said enclosure.

22. A dual energy x-ray method for determining bone density using vertical scanning, comprising:
 providing a gantry positioned at least partially in an enclosure and vertically movable within said enclosure between an upper position and a lower position, said gantry including a source assembly and a detector assembly spaced from each other by patient space and configured to move in unison when said gantry is vertically moved, wherein said source assembly is positioned in said enclosure and said detector assembly is positioned outside said enclosure, and wherein said source assembly includes an x-ray source and transmission window and is configured to emit a fan beam of x-ray radiation that includes high energy x-rays and low energy x-rays toward said detector assembly, the source assembly including an x-ray source and a transmission window, the transmission window configured to serve as a collimator, and wherein said detector assembly produces, from said high and low energy x-rays, dual energy scan data comprising high energy detected x-ray data and low energy x-ray detector data in response to receiving said x-ray radiation from said source assembly;
 providing a redefining aperture also configured to serve as a collimator and positioned between an outer wall of the enclosure and the source assembly for selectively redefining the fan beam emitted by the x-ray source and collimated by the transmission window;
 positioning a patient between said source and detector assemblies for a predefined bone density measurement;
 activating said source assembly to emit said fan beam of x-ray radiation toward said detector assembly; and
 vertically moving said gantry with said source assembly emitting said fan beam of x-ray radiation to scan a selected portion of the patient.

23. The method according to claim 22 further comprising processing scan data received by said detector assembly to determine bone density of the patient relative to said selected scanned portion of the patient.

24. The method according to claim 22, wherein said patient is positioned between said source and detector assemblies for an A/P or P/A spine scan.

25. The method according to claim 22 further comprising:
 changing said position of the patient relative said source and detector assemblies for a different bone density measurement;
 activating said source assembly to radiate said fan beam of x-rays towards said detector assembly; and
 vertically moving said gantry with said source assembly radiating said fan beam of x-rays to scan a different selected portion of the patient.

26. The method according to claim 25 further comprising processing scan data received by said detector assembly to determine bone density of the different selected portion of the patient.

27. The method according to claim 25, wherein said patient is positioned between said source and detector assemblies for a right hip scan.

28. The method according to claim 25, wherein said patient is positioned between said source and detector assemblies for a left hip scan.

29. The method according to claim 25, wherein said patient is positioned between said source and detector assemblies for a lateral spine scan.

30. A method of carrying out a dual energy x-ray study on a patient comprising:

selectively energizing an x-ray tube positioned within an enclosure to generate x-ray radiation that includes high energy x-rays and low energy x-rays, and collimating the x-ray radiation to emit a fan beam of x-ray radiation which spreads more horizontally than vertically;

selectively redefining the collimated fan beam by again collimating the generated and collimated x-ray radiation;

detecting the emitted high energy and low energy x-rays within said fan beam of x-ray radiation with at least one detector positioned outside the enclosure and which is spaced horizontally from the x-ray tube to leave a patient space between the tube and the detector to produce, from the high and low energy x-rays, dual energy x-ray measurements for respective angular positions within said fan beam;

moving said x-ray tube within said enclosure and said detector vertically in a coordinated scanning motion to scan a selected portion of a patient who is in said patient position with said fan beam such that said detector remains aligned with said tube during said scan and produces said dual energy x-ray measurements during the scan; and selectively processing at least the dual energy x-ray measurements produced by the at least one detector to estimate a selected patient characteristic.

31. A method according to claim 30 including carrying out a study of a patient by scanning said fan beam for at least two of an A/P or a P/A scan, a lateral spine scan, a left hip scan and a right hip scan by repositioning the patient in said patient space.

32. The apparatus according to claim 30, wherein said x-ray radiation emitted by said x-ray tube comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

33. A method according to claim 31 in which said collimated beam is a single energy x-ray beam and said collimated beam is detected by said detector which discriminates two energy levels to produce dual energy measurements.

34. A dual energy x-ray method for determining bone density using vertical scanning, comprising:

providing a gantry positioned at least partially in an enclosure and vertically movable within said enclosure between an upper position and a lower position, said gantry including a source assembly and a detector assembly spaced from each other by patient space and configured to move in unison when said gantry is vertically moved, wherein said source assembly is positioned in said enclosure and said detector is positioned outside said enclosure, and wherein said source assembly includes an x-ray source and transmission window and is configured to emit a fan beam of x-ray radiation that includes high energy x-rays and low energy x-rays toward said detector assembly, the transmission window configured to serve as a collimator, and wherein said detector assembly produces, from said high and low energy x-rays, dual energy scan data comprising high energy detected x-ray data and low energy x-ray detected data in response to receiving said x-ray radiation from said source assembly, wherein a redefining aperture, also configured to serve as a collimator, is positioned between an outer wall of the enclosure and the source assembly for selectively redefining the fan beam emitted by the x-ray source and collimated by the transmission window;

positioning a patient between said source and detector assemblies for a predefined bone density measurement;

activating said source assembly to emit said fan beam of x-ray radiation towards said detector assembly;

vertically moving said gantry with said source assembly emitting said fan beam of x-ray radiation to scan a selected portion of the patient;

changing said position of the patient relative said source and detector assemblies and vertically moving said gantry with said source assembly emitting said fan beam of x-ray radiation to scan a different selected portion of the patient without changing said position of said gantry relative said enclosure.

35. The apparatus according to claim 1, wherein an operating voltage applied to said x-ray source is alternated so that said x-ray radiation emitted comprises only said high energy and low energy x-rays.

36. The apparatus according to claim 1, wherein said x-ray source generates a spectrum of x-rays and a filter is used so that said x-ray radiation emitted comprises said high energy and low energy x-rays.

37. The apparatus according to claim 1, wherein said x-ray radiation emitted by said source assembly comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

38. The apparatus according to claim 11, wherein an operating voltage applied to an x-ray source in said source assembly is alternated so that said x-ray radiation emitted comprises only said high energy and low energy x-rays.

39. The apparatus according to claim 11, wherein an x-ray source in said source assembly generates a spectrum of x-rays and a filter is used so that said x-ray radiation emitted comprises said high energy and low energy x-rays.

40. The apparatus according to claim 11, wherein said x-ray radiation emitted by said source assembly comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

41. The apparatus according to claim 17, wherein an operating voltage applied to said x-ray source is alternated so that said x-ray radiation emitted comprises only said high energy and low energy x-rays.

42. The apparatus according to claim 17, wherein said x-ray source generates a spectrum of x-rays and a filter is used so that said x-ray radiation emitted comprises said high energy and low energy x-rays.

43. The apparatus according to claim 17, wherein said x-ray radiation emitted by said source assembly comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

44. The apparatus according to claim 22, wherein an operating voltage applied to said x-ray source is alternated so that said x-ray radiation emitted comprises only said high energy and low energy x-rays.

45. The apparatus according to claim 22, wherein said x-ray source generates a spectrum of x-rays and a filter is used so that said x-ray radiation emitted comprises said high energy and low energy x-rays.

46. The apparatus according to claim 22, wherein said x-ray radiation emitted by said source assembly comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

47. The apparatus according to claim 30, wherein an operating voltage applied to said x-ray tube is alternated so that said x-ray radiation emitted comprises only said high energy and low energy x-rays.

48. The apparatus according to claim 30, wherein said x-ray tube generates a spectrum of x-rays and a filter is used so that said x-ray radiation emitted comprises said high energy and low energy x-rays.

49. The apparatus according to claim 34, wherein said x-ray radiation emitted by said source assembly comprises a spectrum of x-rays, and said detector assembly includes at least one energy radiation detector that absorbs low energy x-rays from said spectrum of x-rays and at least one radiation detector that absorbs high energy x-rays from said spectrum of x-rays to produce said dual energy detected x-rays outputs.

50. The apparatus according to claim 34, wherein an operating voltage applied to said x-ray source is alternated so that said x-ray radiation emitted comprises only said high energy and low energy x-rays.

51. The apparatus according to claim 34, wherein said x-ray source generates a spectrum of x-rays and a filter is used so that said x-ray radiation emitted comprises said high energy and low energy x-rays.

* * * * *